(12) United States Patent
Berglund

(10) Patent No.: US 10,576,046 B2
(45) Date of Patent: Mar. 3, 2020

(54) ORAL COMPOSITION

(71) Applicant: MEDA OTC AB, Solna (SE)

(72) Inventor: Thomas Berglund, Jar (NO)

(73) Assignee: Meda OTC AB (SE)

( * ) Notice: Subject to any disclaimer, the term of this patent is extended or adjusted under 35 U.S.C. 154(b) by 0 days.

(21) Appl. No.: 15/315,974

(22) PCT Filed: Jun. 17, 2015

(86) PCT No.: PCT/EP2015/063518
§ 371 (c)(1),
(2) Date: Dec. 2, 2016

(87) PCT Pub. No.: WO2015/193337
PCT Pub. Date: Dec. 23, 2015

(65) Prior Publication Data
US 2017/0119705 A1    May 4, 2017

(30) Foreign Application Priority Data
Jun. 18, 2014 (NO) .................................. 20140765

(51) Int. Cl.
| A61K 31/155 | (2006.01) |
| A61K 31/32 | (2006.01) |
| A61K 31/315 | (2006.01) |
| A61K 31/722 | (2006.01) |
| A61K 31/30 | (2006.01) |
| A61K 31/14 | (2006.01) |
| A61K 9/00 | (2006.01) |

(Continued)

(52) U.S. Cl.
CPC .......... *A61K 31/155* (2013.01); *A61K 9/0053* (2013.01); *A61K 31/14* (2013.01); *A61K 31/30* (2013.01); *A61K 31/315* (2013.01); *A61K 31/32* (2013.01); *A61K 31/722* (2013.01); *A61K 47/02* (2013.01); *A61K 47/36* (2013.01)

(58) Field of Classification Search
None
See application file for complete search history.

(56) References Cited

U.S. PATENT DOCUMENTS

| 6,344,184 B1 * | 2/2002 | Rolla ....................... A61K 8/27 424/49 |
| 2005/0238602 A1 * | 10/2005 | Modak ..................... A61K 8/36 424/70.11 |
| 2006/0140876 A1 | 6/2006 | Risueno et al. |

(Continued)

FOREIGN PATENT DOCUMENTS

| EP | 0920857 A2 | 6/1999 |
| EP | 1595537 | * 11/2005 |

(Continued)

OTHER PUBLICATIONS

Abstract, Thane et al., J Clin Dent. 2007;18(3):82-6.*

(Continued)

*Primary Examiner* — Karl J Puttlitz

(57) ABSTRACT

The present invention relates to a composition comprising an antibacterial agent in an amount insufficient to provide antibacterial effect, a physiologically acceptable divalent metal ion in a very low concentration and a physiologically acceptable polymer for preventing and/or treating halitosis, bad breath, dry mouth or sore throat.

6 Claims, 3 Drawing Sheets

(51) Int. Cl.
*A61K 47/02* (2006.01)
*A61K 47/36* (2006.01)

(56) References Cited

U.S. PATENT DOCUMENTS

2012/0263657 A1  10/2012  Doyle et al.
2012/0301408 A1  11/2012  Baker et al.

FOREIGN PATENT DOCUMENTS

| WO | 2004011011 | * | 2/2004 |
| WO | 2005074947 | * | 8/2005 |
| WO | 2006074359 A2 | | 7/2006 |
| WO | 2009/106963 | * | 9/2009 |

OTHER PUBLICATIONS

Written Opinion of the International Searching Authority for PCT/EP2015/063518, 5 pages.
International Search Report for PCT/EP2015/063518, dated Oct. 7, 2015, 3 pages.

* cited by examiner

Aerobe and anaerobe culturing of full saliva i) Aerobe culturing of full saliva
with 20μl of solution A in the well
(0.049% CHX + 0.049% Zn2+
+ 0.1% chitosan); no inhibition.

ii) Anaerobe culturing of full saliva
with 20μl of solution A in the well
no inhibition.

iii)Anaerobe culturing of full
saliva with 20ul of solution II
in the well (0.025% CHX + 0.3% Zn2+);
10 mm inhibition zone

ORAL COMPOSITION

FIELD OF THE INVENTION

The present invention relates to a composition comprising an antibacterial agent in an amount insufficient to provide antibacterial effect, a physiologically acceptable divalent metal ion in a very low concentration and a physiologically acceptable polymer for preventing and/or treating halitosis, bad breath, dry mouth or sore throat.

BACKGROUND OF THE INVENTION

Halitosis, is breath that has an unpleasant odor. This odor can strike periodically or be persistent, depending on the cause. Halitosis is primarily caused by some of the bacteria forming the natural bacterial flora in the oral cavity, particularly bacteria located in the crypts at the back of the tongue and in periodontal pockets. Said bacteria produce by anaerobic metabolism volatile sulfur compounds which is mainly hydrogen sulfide and methyl mercaptan giving rise to the unpleasant odor.

It is well known in the art that zinc ions possess a certain antibacterial activity and to some extent reduce the volatile sulfur compounds production in the oral cavity. Antibacterial agents like e.g. chlorhexidine, cetylpyridinium chloride and also chitosan have been suggested and investigated in order to reduce the production of volatile sulfur compounds, and thereby diminish the unpleasant odor, and has been described in:

Young et al. (Eur J Oral Sci 2003; 111:400-404) discloses inhibition of orally produced volatile sulfur compounds by Zinc, chlorhexidine or cetylpyridinium chloride and the effect of the concentration.

Roldan et al. (J Clin Periodontol 2004; 31:1128-1134) discloses the comparative effects of different chlorhexidine mouth-rinse formulations on volatile sulphur compounds and salivary bacterial counts.

Verkaik et al. (J Dentistry 2011; 39:218-224) discloses the efficacy of natural antimicrobials in toothpaste formulations against oral biofilms in vitro.

NO 307168 discloses that an anti-volatile sulfur compounds effect of zinc ion is mainly directed against hydrogen sulfide production and to a far lesser extent against the production of methyl mercaptan which explain the incomplete elimination of the halitosis. However, when a combination of zinc ions and low concentration of certain cationic antibacterial agents were used the combination inhibited both hydrogen sulfide and methyl mercaptan formation in a synergistic way.

The microbial flora in the oral cavity is a fine-tuned protective system playing an important part in the immune system, and in decomposing the nutrition we eat, and is further responsible for keeping the digestion system in balance. A shift in this delicate system due to antibacterial activity from antibacterial agents may lead to fungus growth, soar mouth, diarrhea etc. Said agents may also cause dental stain.

In work leading up to this invention the inventor surprisingly detected that by combining an antibacterial agent in an amount insufficient to provide antibacterial effect together with a physiologically acceptable divalent metal ion in a very low concentration and a physiologically acceptable polymer, the composition reduces the sulfur gasses in a synergistic way without any interference with the microbial flora in the oral cavity. The composition was demonstrated to prevent and/or treat halitosis, bad breath, dry mouth or sore throat.

Zinc lozenges have been suggested as a cure for common cold (Eby III et al. Medical Hypotheses 2010; 74:482-92). This is still controversial and the zinc concentration used for this purpose is much higher than in the composition of the present invention and is likely to be caused by an antibacterial and/or antiviral effect. It is thus highly surprising and unexpected that the present invention where proved to be efficient against sore throat even though no apparent antibacterial effect is present. The mechanism for this is still unknown.

It is therefore believed that the present invention will be a safer and more effective composition in preventing and/or treating halitose, bad breath, dry mouth or sore throat.

The result of chlorhexidine in a concentration of 0.0049% alone shows a reduction in hydrogen sulphide gas of 12% after one hour, 8% reduction after 2 hours, and 7% after 3 hours.

The result of chlorhexidine in a concentration of 0.0049% in combination with $Zn^{2+}$ in a concentration of 0.049% shows a reduction in hydrogen sulphide gas of 39% after one hour, 26% reduction after 2 hours, and 17% reduction after 3 hours.

The result of chlorhexidine in a concentration of 0.0049% in combination with $Zn^{2+}$ in a concentration of 0.049% and chitosan in 0.1% shows a reduction in hydrogen sulphide of 58% after one hour, 41% after reduction after 2 hours and 32% after 3 hours.

Figure 2:
Figure 2:
Figure 2:
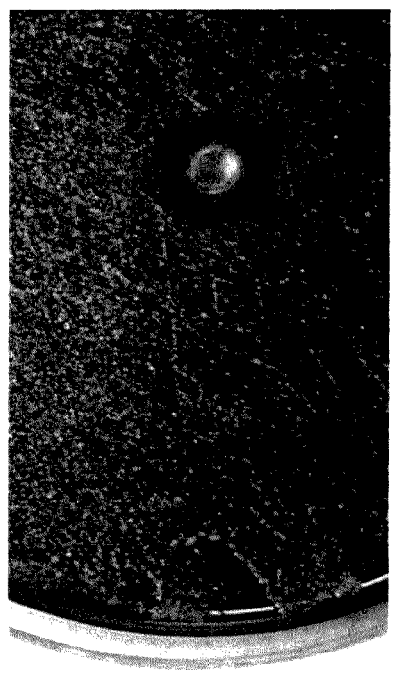

FIG. 2: Illustrates aerobe and anaerobe culturing of full saliva
  i) Aerobe culturing of full saliva with 20 ul of solution A (0.0049% CHX+0.049% $Zn^{2+}$+0.1% chitosan) in the well shows no inhibition.
  ii) Anaerobe culturing of full saliva with 20 ul of solution A in the well; shows no inhibition.
  iii) Anaerobe culturing of full saliva with 20 ul of solution B (0.025% CHX+0.3% $Zn^{2+}$) in the well shows a 10 mm inhibition zone.

DETAILED DESCRIPTION OF THE INVENTION

The aim of the present invention is to provide a composition showing maximum inhibitory effect on the volatile sulfur gasses causing halitose, bad breath dry mouth or sore throat with a minimum of inhibitory effect on the normal oral micro flora. The present invention provides therefore a composition comprising an antibacterial agent in an amount insufficient to provide antibacterial effect, a physiologically acceptable divalent metal ion in a very low concentration and a physiologically acceptable polymer for preventing/treating halitosis, bad breath, dry mouth or sore throat.

Antibacterial agents such as bis-biguanide and quaternary ammonium compounds is presently being used in oral composition to provide antibacterial effect.

The inventor surprisingly detected that by combining an antibacterial agent in an amount insufficient to provide antibacterial effect, a physiologically acceptable divalent metal ion in a very low concentration and a physiologically acceptable polymer, the composition had the ability to reduce the sulfur gasses in the oral cavity and preventing and/or treating halitosis, bad breath, dry mouth or sore throat.

Further it was surprisingly identified that chitosan performed a synergistic effect together with zinc and chlorhexidine in very low concentrations under slightly acidic condition.

Chitosan is a polysaccharide, derived from the deacetylation of chitin which is a naturally occurring polymer and nature's second most abundant polymer after cellulose. Chitosan has been shown to be biocompatible and biodegradable and to have some antibacterial effect although the precise antibacterial mechanism is still unknown. However, chitosan also has strong bioadhesive properties, binding to negatively charged surfaces and structures.

In one embodiment of the present invention no antibacterial effect can be demonstrated and the effect of the chitosan or its derivative in the composition of the present invention is therefore believed to enhance the effect by binding to the antibacterial agent, e.g. chlorhexidine and places it close to the bacteria on negative loaded surfaces where the volatile sulfur compositions are formed and linking the antibacterial agent, e.g. chlorhexidine to the zinc for it to exert its action which is believed to be cutting the SH bonds.

The effect of chitosan in regard to Zn is believed to be that chitosan binds to the mucosa and negative loaded tooth surfaces and thereby prolong the presence and the effect of zinc in the oral cavity.

In Experiment 1 three different compositions were tested comprising the following combinations:
Composition 1: Chlorhexidine in a concentration of 0.0049% by weight.
Composition 2: Chlorhexidine in a concentration of 0.0049% by weight in combination with $Zn^{2+}$ in a concentration of 0.049% by weight.
Composition 3: Chlorhexidine in a concentration of 0.0049% by weight in combination with $Zn^{2+}$ in a concentration of 0.049% by weight and chitosan in a concentration of 0.1% by weight.

Figure 1:
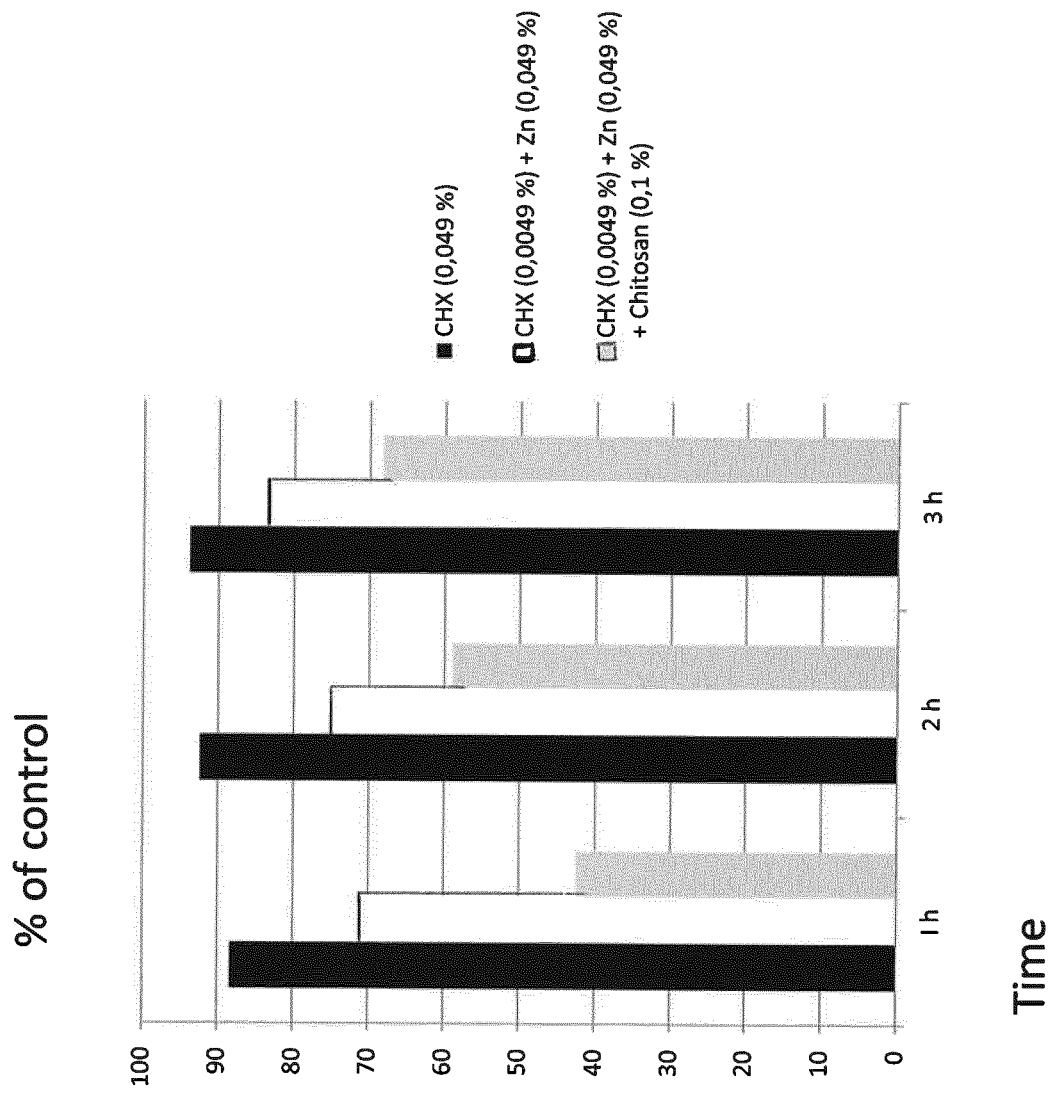
FIG. 1: Illustrates the amount hydrogen sulphide in percentage of the control. The control is the amount of hydrogen sulphide measured in a gas chromatograph after rinsing with cysteine.

As can be seen from Example 1 and FIG. 1 it is clearly demonstrated that composition 3 was the most effective in reducing the volatile sulphur compounds. A reduction of 58% after one hour, 41% reduction after 2 hours and 32% reduction after 3 hours were achieved, which is an increase in effect of 19%, 15% and 15% respectively compared to solution 2. Compared to solution 1 the differences in the effect were 46%, 33 and 25% respectively.

The combination of Chlorhexidine, $Zn^{2+}$ and chitosan described in composition 3 was shown to have a synergistic effect compared to compositions 1 and 2. It was further demonstrated in Example 2 that composition 3 in Example 1 comprising chlorhexidine in a concentration of 0.0049% in combination with $Zn^{2+}$ in a concentration of 0.049% and chitosan in a concentration of 0.1% which are concentrations insufficient to show an antibacterial effect, did not have any influence on the bacteria flora in the oral cavity.

In Example 1 chlorhexidine has been tested as an antibacterial agent but any agent or its salt thereof selected from the bis-biguanide and quaternary ammonium compounds or any combinations thereof may be utilized.

As a physiologically acceptable divalent metal ion Cu or Sn may be selected instead of Zn. Said metal ion may be present in form of a salt, a chelate or any mixture thereof.

A physiologically acceptable polymer like a polysaccharide or a polysaccharide derivative other than chitosan may be utilized in the composition of the present invention.

A physiologically acceptable organic acid having a pKa in the range of 2-6 and selected from the group of benzoic acid, glycine or any mixture thereof may be used alone or in combination with a physiologically acceptable polymer.

The pH of the composition may be in the range of about 2.5 to about 9.0, preferably about 2.5 to about 6.5.

The composition may further comprise at least one fluoride source. The at least one fluoride source may be present in the composition in an amount of about 0.005%-2.5% by weight. The at least one fluoride source may be a soluble inorganic fluoride salt, a soluble organic fluoride salt, HF or any mixture thereof.

In Example 2 solutions A and B were tested for their ability to provide an antimicrobial effect. Microorganisms from the oral cavity were cultured on petri dishes and subjected to:
Solution A comprising: chlorhexidine (0.0049% by weight), $Zn^{2+}$ (0.049% by weight) and chitosan (0.1% by weight); and
Solution B comprising: chlorhexidine (0.025% by weight) and $Zn^{2+}$ (0.3% by weight).

The results of the test shown in Table 1 and FIG. 2 i) and ii) demonstrate that Solution A comprising chlorhexidine (0.0049% by weight), $Zn^{2+}$ (0.049% by weight) and chitosan (0.1% by weight) did not inhibit growth of the microorganism with the exception from two fungi strains; *C. albicans* and *C. parapsil*, said fungi are however, not involved in the production of sulfur gasses.

Solution B comprising chlorhexidine (0.025% by weight) and $Zn^{2+}$ (0.3% by weight) inhibits growth as can be seen from Table 1 and FIG. 2 iii).

The technical effect of the composition of the present invention may therefore be described as a reduction of the sulfur gases by neutralizing the gasses. The mechanism behind is believed to be that the antibacterial agent cuts the S—H binding of the sulfur gas; the Zn and probably also chitosan precipitate the sulfur to sulfide which is swallowed and then excreted. The bacterial/microorganism flora of the oral cavity will stay intact due to the low concentrations of the antibacterial agents.

In Example 3 the composition of the present invention is shown to also have an effect on sore throat as the test subjects experienced relief from the nuisance few hours after the first rinse. The mechanism behind this effect is unknown.

Accordingly an aspect of the present invention relates to a composition comprising an antibacterial agent, a physiologically acceptable divalent metal ion and a physiologically acceptable polymer, the antibacterial agent may be selected from bis-biguanide and quaternary ammonium compounds or any combination thereof; and the physiologically acceptable divalent metal ion may be selected from the group consisting of Zn, Cu and Sn.

As used herein "the antibacterial agent" refers to an agent that either kills or inhibits the growth of a microorganism.

In further embodiments of the composition the antibacterial agent may be chlorhexidine or a salt thereof. The chlorhexidine may be present in the composition in an amount of 0.001%-1% preferably 0.002-0.5%, more preferably 0.004-0.01 by weight.

In a further embodiment of the composition the antibacterial agent may be present in the composition in amounts insufficient to effectively kill or inhibit growth of the bacteria in the oral cavity.

As used herein "amounts insufficient to provide antibacterial effect" refers to a concentration or a dose of an agent that is unable to either kills or inhibit the growth of a microorganism.

In one or more embodiments of the composition the physiologically acceptable salt of a divalent metal ion and/or a divalent metal ion chelate may be present in in an amount of 0.01%-0.5% by weight, or in an amount of 0.01%-0.049% by weight, or in an amount of 0.01%-0.04% by weight.

In one or more embodiments of the composition the physiologically acceptable salt of a divalent metal ion and/or a divalent metal ion chelate may be present in the composition in an amount of 0.01%-0.19% by weight, or 0.01%-0.15% by weight. Further the physiologically acceptable divalent metal ion may be present in form of a salt, a chelate or any mixture thereof.

In one or more embodiments of the composition the physiologically acceptable polymer may be present in the composition in an amount of 0.1%-2% by weight and may further be in an encapsulated form, in the form of micro particles or in the form of nano particles or any mixture thereof. The physiologically acceptable polymer may further be in an encapsulated form where the polymer may be encapsulated in an aqueous solution at a pH of about 3-7. Further the physiologically acceptable polymer may be a polysaccharide or a polysaccharide derivative. The physiologically acceptable polymer may be chitosan or a chitosan derivative. The chitosan or the chitosan derivative may be present in the composition in amounts insufficient to provide antibacterial effect.

In one embodiment of the composition, the composition may be an aqueous solution or a gel.

In one embodiment of the composition, the composition may have a pH of about 2.5-6.5.

In one embodiment of the composition the antibacterial agent may be selected from bis-biguanide and quaternary ammonium compounds or any combination thereof and may be present in the composition in an amount of 0.001%-1% by weight; the physiologically acceptable divalent metal ion may be Zn, Cu or Sn and may be present in the composition in an amount of 0.01%-0.5% by weight; and the physiologically acceptable polymer may be a polysaccharide or a polysaccharide derivative and may be present in the composition in an amount of 0.1%-2% by weight.

In one further embodiment the physiologically acceptable polymer may be chitosan or a chitosan derivative which may be present in the composition in an amount of 0.1%-2%.

In one embodiment the composition is preventing and/or treating halitosis.

In one embodiment the composition is preventing and/or treating bad breath.

In one embodiment the composition is preventing and/or treating dry mouth.

In one embodiment the composition is preventing and/or treating sore throat.

In one embodiment the composition is preventing and/or treating sore throat caused by a viral infection or a bacterial infection.

In one embodiment the composition may be maintained in the oral cavity for about 10-120 seconds and then discharged from the mouth.

In one embodiment the composition may be gurgled for about 10-120 seconds and then discharged from the mouth.

Having now fully described the present invention in some detail by way of illustration and example for purpose of clarity of understanding, it will be obvious to one skilled in the art that same can be performed by modifying or changing the invention by a wide and equivalent range of conditions, formulations and other parameters thereof, and that such modifications or changes are intended to be encompassed within the scope of the appended claims.

EXAMPLES

Example 1

Measuring Oral Malodour ($H_2S$) in Test Subjects

The compositions to be tested in this experiment were:

Composition 1: Chlorhexidine in a concentration of 0.0049%.

Composition 2: Chlorhexidine in a concentration of 0.0049% in combination with $Zn^{2+}$ in a concentration of 0.049%.

Composition 3: Chlorhexidine in a concentration of 0.0049% in combination with $Zn^{2+}$ in a concentration of 0.049% and
chitosan in a concentration of 0.1%.

On the test day, the test subjects (three subjects) were instructed to refrain from their normal oral hygiene routine following breakfast. Oral malodour was introduced in the subjects by rinsing for 30 sec. with a 5 ml of 6mM L-cysteine solution (pH 7.2). The subjects then kept their mouth closed for 1 min. 30 sec. after which baseline mouth air samples were recorded by aspirating mouth air using a 10-ml syringe connected to the outlet of the auto injector of a gas chromatograph. The volatile sulphur compound $H_2S$ were then measured directly. Immediately after this procedure the subject rinsed for 1 min with 10 ml of one of the test solutions (compositions 1 to 3) and the solutions were expectorated. Cysteine rinsing and mouth air analyses were repeated at 1 h, 2 h and 3 h after rinsing with the respective solutions. No eating drinking or smoking was permitted during the test period.

Results

The results can be seen in FIG. 1 and demonstrates clearly that the solution comprising chlorhexidine in a concentration of 0.0049% in combination with
$Zn^{2+}$ in a concentration of 0.049% and chitosan in a concentration of 0.1% was the most effective in reducing the volatile sulphur compound where a reduction of 58% after one hour, 41% reduction after 2 hours, and 32% after 3 hours was achieved, which is an increase of 19%, 15% and 15% respectively compared to the solution comprising the chlorhexidine in combination with $Zn^{2+}$. Compared to the solution comprising chlorhexidine only, the differences in the percentage effect were 46%, 33 and 25% respectively.

Example 2

Microbiological Testing of a Solution (A) Consisting of CHX (0.0049%) and $Zn^{2+}$ (0.049%) and Chitosan (0.1%) and Compared to a Solution (B) Consisting of CHX (0.025%) and $Zn^{2+}$ (0.3%)

Microorganisms from the oral cavity were cultured on petri dishes and subjected to:

Solution A: CHX (0.0049% by weight) and $Zn^{2+}$ (0.049% by weight) and chitosan (0.1% by weight) and Solution B: CHX (0.025% by weight) and $Zn^{2+}$ (0.3% by weight), and deposited in a well in the middle of the dish respectively. Inhibition activity could be measured as an inhibition zone around the well (see FIG. 2 iii). The results from the tests are presented in Table 1.

TABLE 1

| Microorganism/Culturing | Extension of inhibition zone (in mm) | |
| --- | --- | --- |
| | Solution A | Solution B |
| 1. *Streptococcus mutans* | 0 | 12 |
| 2. *Escherichia coli* | 0 | 10 |
| 3. Saliva aerobe culturing | 0 | 11 |
| 4. *Enterococcus faecium* | 0 | 8 |
| 5. *Staphylococcus aureus* | 0 | 11 |
| 6. *Candida albicans* | 5 | 6 |
| 7. *Candida parapsil* | 6 | 13 |
| 8. Saliva anaerobe culturing | 0 | 10 |
| 9. *Aggregatibacter actinomycetemcomitans* anaerobe culturing | 0 | 0 |

Ad. 2. and 8. Samples of 0.5 ml of unstimulated whole saliva were collected in a sterile graduated test tube. In the laboratory, samples were dispersed (60 s of vortexing), serially diluted and plated on Trypticase soy agar (BBL Microbiological Systems, Cockeysville, Md., USA) added 5% sheep blood, 0.0005% hemin and 0.00003% menadione.

Each agar contained a standardized well in the center that was filled with either solution A or B
- 20 ul of solution A (0.049% CHX+0.049% $Zn^{2+}$+0.1% chitosan) was applied in the well.
- 20 ml of solution B (0.025% CHX+0.3% $Zn^{2+}$) was applied in the well.

They were both subsequently incubated as follows:

Ad.3. Anaerobe incubation: Incubated at 37° C. in anaerobic chamber (90% $N_2$, 5% $H_2$, 5% $Co_2$) (Anoxomat, WS9000; Mart; Lichtenvoorde, The Netherlands) for 7-14 days.

Ad. 8. Aerobic incubation: Incubated aerobically at 37° C. for 24-48 h

The rest was cultivated on selective media, as follows:

Ad 1. *S. mutans*, Anaerobe culturing as above for 3 days on Mitis-salivarius-bacitracin agar plates. *S. Mutans* were identified as small mucoid colonies.

Ad 2 *E. coli* cultivated on Eosin Methylene blue agar (EMB agar) for 3 days in air at 37° C. Colonies have a dark center and a greenish metallic sheen.

Ad. 4. *E. faecium*. Incubated in air at 37° C. for 3 days on a Cephalexin-aztreonam-arabinose agar (CAA) (Ford et al 1994).

Ad 5. *S. aureus*. Incubated in air at 37° C. for 3 days on *Staphylococcus* agar plates and distinguished from *S. epidermidis* by their ability to degrade DNA on DNA agar plates (Difco).

Ad. 6. *C. albicans*. Cultivated on Sabouraud T agar plates for 3 days in air at 37° C. They were identified as lusterless and creamy white-pink, or pink, colonies.

Ad 7. *C. parapsil*. Cultivated on Sabouraud's dextrose agar for 3 days in air at 37° C.

Ad.9. A.a. Anaerobe incubation (described above) for 3-5 days on trypticase soy-serum bacitracin-vancomycin (TSBV) medium for selective isolation of A.a. (Slots 1982)

Results:

The result of the test shown in Table 1 and FIG. 2 i) (aerobe culturing) and ii) (anaerobe culturing) demonstrates that Solution A comprising chlorhexidine (0.0049% by weight), $Zn^{2+}$ (0.049% by weight) and chitosan (0.1% by weight) did not inhibit growth of the microorganism with the exception of two fungus strains; *C. albicans* and *C. parapsil*, said fungi are however, not involved in the production of sulfur gasses.

Solution B comprising chlorhexidine (0.025% by weight) and $Zn^{2+}$ (0.3% by weight) Inhibits growth measured as a an extension of inhibition zone in mm, can be seen from Table 1 and FIG. 2 iii).

Example 3

Mouth/throat Rinsing with the Composition of the Present Invention had a Positive Effect on Sore Throat Five test subjects suffering of sore throat rinsed/gurgled their mouth/throat twice a day (in the morning and in the evening) for 1 min with a solution comprising the composition of the present invention. After rinsing/gurgling the solution was expectorated.

The solution comprising:

Chlorhexidine in a concentration of 0.0049% in combination with $Zn^{2+}$ in a concentration of 0.049% and chitosan in a concentration of 0.1%.

Subject 1 had suffered from sore throat for two days
Subject 2 had suffered from sore throat for one day
Subject 3 had suffered from sore throat for two days
Subject 4 had suffered from sore throat for three days
Subject 4 had suffered from sore throat for one day Results Within two days of gurgling twice a day all symptoms of a sore throat disappeared in all test subjects.

I claim:

1. An oral solution composition comprising about 0.0049 wt % chlorhexidine or a salt thereof; about 0.049 wt % of physiologically acceptable divalent metal ion selected from the group consisting of Zn, Cu, or Sn; and about 0.1 wt % chitosan.

2. The composition of claim 1, further comprising at least one fluoride source.

3. The composition of claim 2, wherein the at least one fluoride source is present in the composition in an amount of about 0.005%-2.5% by weight.

4. The composition of claim 3, wherein the at least one fluoride source is selected from the group consisting of a soluble inorganic fluoride salt, a soluble organic fluoride salt, HF, and a mixture thereof.

5. The composition of claim 1, wherein the physiologically acceptable divalent metal ion is Zn.

6. A method for preventing or treating halitosis, comprising administering an effective amount of the oral solution composition of claim 1 to the oral cavity of a subject in need thereof.

* * * * *